United States Patent [19]
Picha et al.

[11] Patent Number: 5,082,000
[45] Date of Patent: Jan. 21, 1992

[54] BIOPSY FORCEPS WITH CALDE CONTROLLED JAWS

[75] Inventors: George J. Picha, Independence; Dean J. Secrest, Euclid, both of Ohio

[73] Assignee: Applied Medical Technology, Inc., Independence, Ohio

[21] Appl. No.: 619,733

[22] Filed: Nov. 29, 1990

[51] Int. Cl.$^5$ .............................................. A61B 10/00
[52] U.S. Cl. ..................... 128/751; 606/171; 606/206
[58] Field of Search ............... 128/750, 751, 752, 753, 128/754, 755; 604/22; 606/167, 171, 170, 174, 205, 206, 207, 208; 30/188, 182, 191, 193, 175

[56] References Cited

U.S. PATENT DOCUMENTS

| | | | |
|---|---|---|---|
| 3,895,636 | 7/1975 | Schmidt | 128/305 |
| 4,043,323 | 8/1977 | Kamiya | 128/4 |
| 4,669,471 | 6/1987 | Hayaski | 606/205 |
| 4,721,116 | 1/1988 | Schintgen et al. | 128/751 |
| 4,887,612 | 12/1989 | Esser et al. | 128/751 |
| 4,896,678 | 1/1990 | Ogawa | 128/751 |
| 4,982,727 | 1/1991 | Sato | 128/4 |

Primary Examiner—Max Hindenburg
Assistant Examiner—Guy V. Tucker
Attorney, Agent, or Firm—Pearne, Gordon, McCoy & Granger

[57] ABSTRACT

A pair of biopsy forceps for capturing, by remote operation, a sample of tissue from an internal location in a patient. The device includes a flexible sheath with a control wire extending therethrough, a pair of jaws movable by the control wire to capture a sample of tissue, and a manual operating means connected at the outer end of the sheath for extending and retracting the control wire. The jaws are mounted at the ends of tongs pivotally mounted in an end housing for movement between open and closed positions. The control wire is connected to lever arms at the rearward end of the tongs by means of two cable lengths connected between the wire and the rearward ends of the lever arms in such a way as to form an effective extension of the respective lever arm.

16 Claims, 4 Drawing Sheets

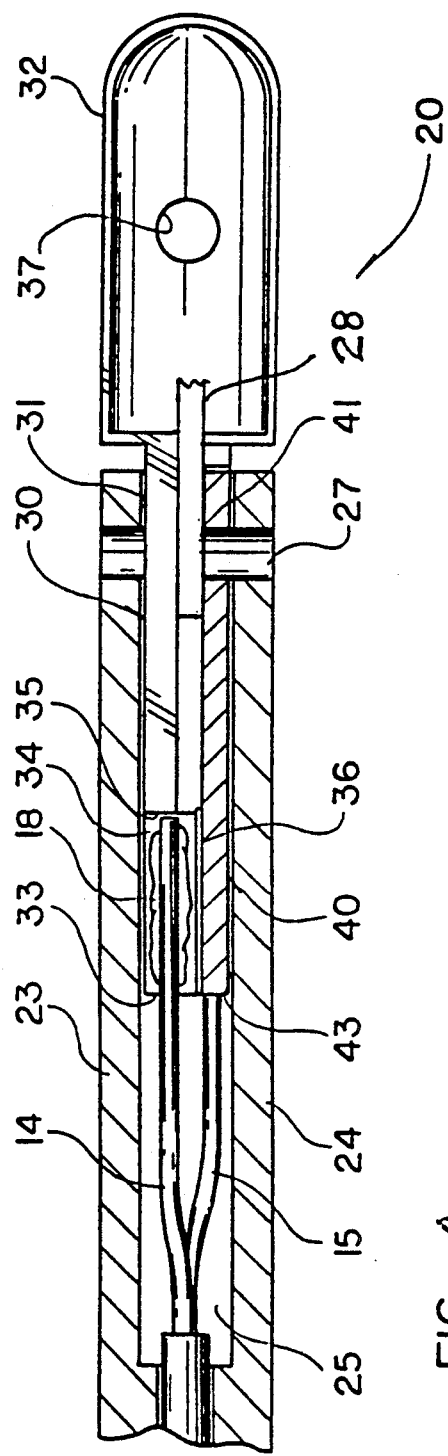
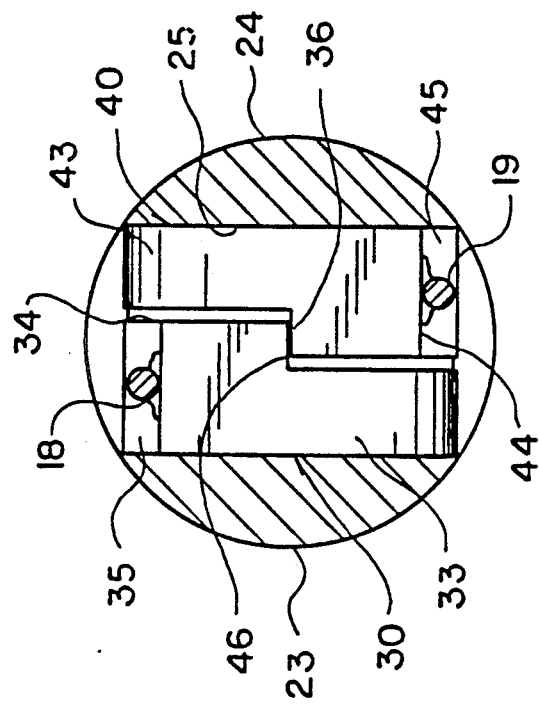
FIG. 4
FIG. 5

BIOPSY FORCEPS WITH CALDE CONTROLLED JAWS

BACKGROUND OF THE INVENTION

This invention relates to biopsy forceps for use in various medical applications, wherein a remotely operable pair of pivotally interconnected levers or tongs with cups or jaws at their outer ends are carried at the end of a thin, elongated sheath or tube. The cups or jaws are adapted to be inserted in a patient while in a closed position and moved to a predetermined internal location. While so positioned, they are manipulated by medical personnel using a control wire extending through the sheath, to capture a sample of tissue. More particularly, the invention provides a unique, simplified operating mechanism for the levers or tongs that minimizes the space required for manipulating the instrument and that renders the device practically disposable in order to reduce the risk of infection that could occur from reuse of the instrument.

Various types of biopsy forceps are currently in use in the medical field, such as in endoscopic procedures. These devices generally include gastroscopes, colonoscopes, sigmoidoscopes, and bronchoscopes, for example. They generally include a pair of levers or tongs that pivot relative to one another between open and closed positions to bring a pair of cup-shaped jaws together to capture a sample of tissue. The instrument also includes a long, resilient, flexible sheath that may be from 100 to 250 centimeters in length.

The head assembly that includes the jaws is carried at the end of the flexible sheath and is inserted in the patient at a desired position in accordance with the procedure to be performed. The jaws are closed during the insertion. When the head assembly is suitably positioned, the jaws are opened by the medical operator, using an elongated wire or cable that extends through the sheath. The operator then closes the jaws, using the control wire or cable to capture a sample of tissue between the jaws. In some cases, the instrument has a barbed needle extending forwardly of the open jaws and located between them to "spear" a sample of tissue and effectively "pull" it between the jaws as they close. The jaws are relatively sharp to enable the sample to be cut free from the surrounding tissue.

The biopsy forceps currently in use are generally of complicated design, with numerous components and, as a consequence, are quite expensive. More importantly, these instruments must be carefully sterilized after each use to enable the device to be used safely with another patient. The sterilizing procedures generally include immersing the contaminated biopsy forceps in chemical sterilizing solutions and/or placing the device in an autoclave. Unfortunately, these conventional sterilizing procedures have recently been found to be imperfect and, upon occasion, the instruments, when reused, have caused the transmission of serious, and even life-threatening, infections. Of particular concern is the risk of transmission of the AIDS virus (acquired immunity deficiency syndrome) or hepatitis B viruses. Also, in some instances, the extreme temperatures often present in an autoclave may cause damage and/or warping of the instrument in such a way as to prevent its proper operation.

As a result of the above considerations, it would appear desirable to have the biopsy forceps so designed and assembled as to make it practical to dispose of them after each use. This would be impractical unless the design of the forceps is sufficiently simplified that disposability becomes cost-effective.

SUMMARY OF THE INVENTION

It is among the objects of the present invention to provide biopsy forceps of simplified design and construction in order to use the device as a disposable instrument that will be discarded after only one use.

Another object of the invention is to improve the operating capability of biopsy forceps by increasing the mechanical advantage obtained in the mechanism used to capture and cut away a sample of tissue.

A further object is to assure that a pair of biopsy forceps may be moved to a closed, tissue-capturing condition by a remote operating mechanism without applying excessive force to the jaws or cups once they have closed and captured the tissue sample.

Still another object of the invention is to reduce the number of parts required and the time involved in the manufacture and assembly of biopsy forceps.

These and other objects and advantages are achieved with the unique biopsy forceps constructed in accordance with the present invention. The forceps include as their primary components a flexible sheath, a control wire or cable extending through and movable within the sheath, a pair of cup-shaped jaws movable by the control wire or cable to a closed position to capture a sample of tissue, and a manual operating means connected at the rearward end of the sheath for extending and retracting the control wire or cable linearly relative to the sheath.

In accordance with the invention, the biopsy forceps further include an end housing connected to the forward end of the sheath and defining a central passage at its rearward end for receiving the control wire. The end housing also has a pair of forwardly extending bifurcations defining a slot therebetween that communicates with the central passage. A pivot pin is located in the forward end of the slot extending across the slot perpendicular to the bifurcations.

A pair of tongs or levers are pivotally connected to the forward end of the housing and carry a pair of jaws at their outer ends, as indicated above. The tongs have rearwardly extending lever arms whereby the tongs may be moved between a closed position, with the jaws closed, and the lever arms brought together in adjacent relationship, and an open position wherein the jaws are open and the lever arms are angularly spaced on opposite sides of the end housing. A pair of relatively stiff, flexible cable lengths are connected at their inner ends to the control wire to provide a pair of forward extensions from the wire and are rigidly connected at their outer ends to the lever arms in coextensive relationship therewith so that at least a portion of each cable length forms an extension of the respective lever arm.

When the control wire is retracted by the manual operating means, the lever arms are moved to their closed position, wherein the cable lengths are relatively unflexed. When the control wire is extended by the manual operating means, the cable lengths flex radially outward in a bulging manner, due to the compressive force applied by the control wire, so as to move the lever arms in opposite directions to their open positions. The outward flexing serves both to apply leverage to the lever arms and to provide an effective extension of the lever arms.

BRIEF DESCRIPTION OF THE DRAWINGS

FIG. 4 is a cross-sectional view, on an enlarged scale, taken on the line 4—4 of FIG. 2; and FIG. 5 is a cross-sectional view, on an enlarged scale, taken on the line 5—5 of FIG. 2.

DESCRIPTION OF THE PREFERRED EMBODIMENT

Figure 1:
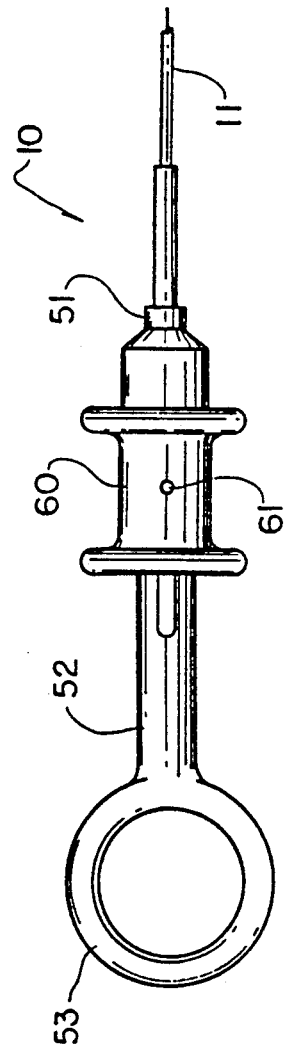
FIG. 1 is an elevational view illustrating a pair of biopsy forceps embodying the invention and showing the jaws of the head assembly in their open position.
Figure 1:
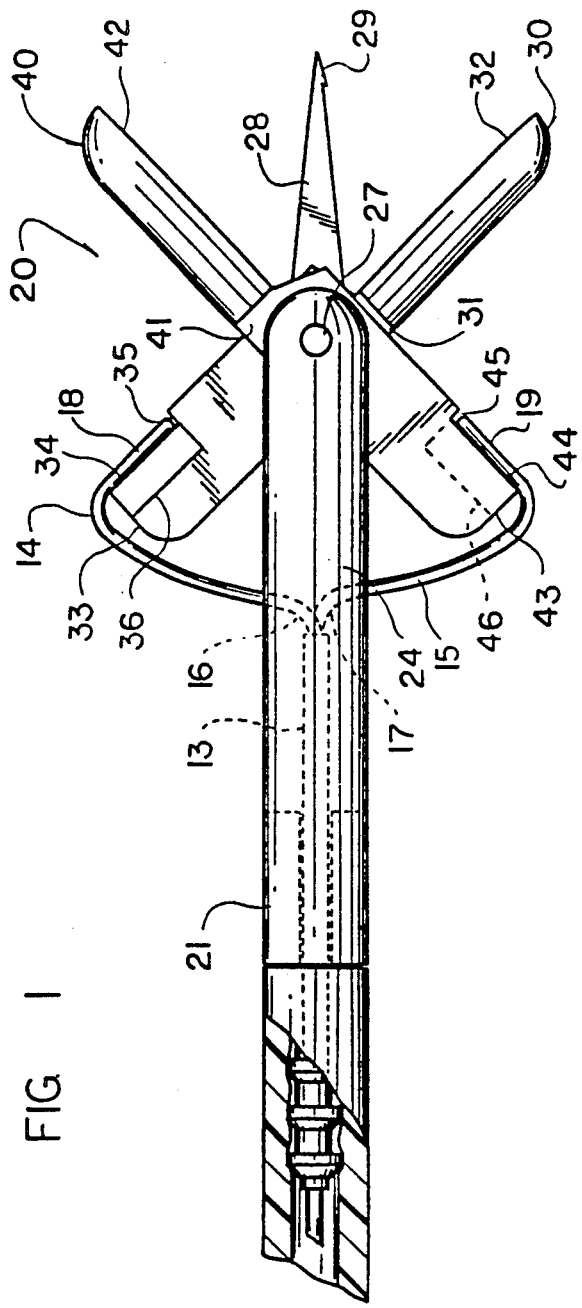
Figure 2:
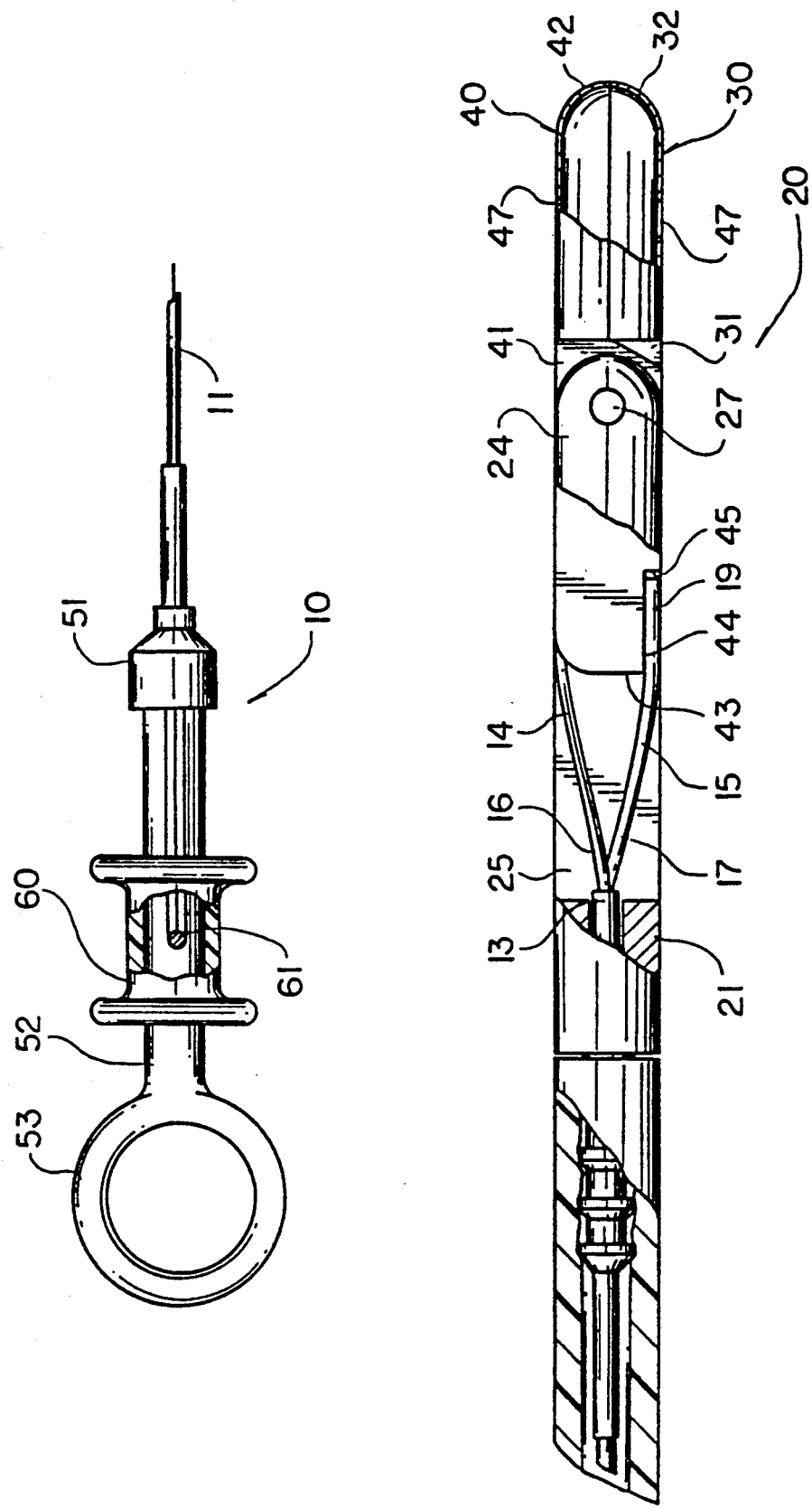
FIG. 2 is an elevational view similar to FIG. 3, showing the jaws of the head assembly pivoted to their closed position, and with parts broken away and shown in section for the purpose of illustration.

Referring more particularly to the drawings, and initially to FIGS. 1 and 2, there is shown in broken elevation a pair of biopsy forceps 10 embodying the invention, and including as their principal components an elongated, hollow sheath 11 with a longitudinally movable control wire 12 located therein. The hollow sheath 11 may be from 100 to 250 centimeters in length, depending upon the particular endoscopic procedure for which the particular embodiment of the instrument is designed. While relatively stiff, the sheath 11 is sufficiently flexible to accommodate the irregular path through which the sheath must pass when inserted in a patient or endoscope. It is preferably formed of polypropylene or TEFLON tubing, and has inner and outer diameters of 0.08 inch and 0.035 inch, respectively.

The control wire is formed of relatively stiff, 0.018 inch diameter, stainless steel with a Teflon coating and is sufficiently flexible to accommodate the directional changes occurring during insertion.

A head assembly 20 is located at the forward end of the sheath and an operating assembly 50 is located at the rearward end. The head assembly is adapted for location at a predetermined position inside the patient, and may be manipulated to capture a sample of tissue which is separated and then removed from the patient for analysis. The operating assembly 50 is adapted to enable the operator to manipulate the head assembly externally of the patient.

Located at the forward end of the control wire 12 is a stainless steel Y-connector 13 which serves to connect the control wire 12 to a pair of stiff, flexible cable lengths 14 and 15 with their rearward ends 16 and 17 secured to the connector in a generally parallel relation to the end of the control wire 12.

The front ends 18 and 19 of the cable lengths are used to operate the head assembly 20 in a manner to be described below. The cable lengths may be, for example, 0.012 inch wound wire cable.

The head assembly 20 includes a relatively thin, elongated, generally cylindrical housing 21 formed of metal, with a hollow connector plug 22 at its rearward end adapted to be rigidly connected to the hollow sheath 11. The hollow connector plug is formed with circumferential ribs or barbs, as shown in FIG. 2, to assure a firm connection. The respective end of the hollow sheath is provided with internal threads to facilitate the connection. During attachment, the end of the sheath is turned so that the internal threads engage the circumferential ribs or barbs on the plug 22 and, although a threaded connection is not achieved, the result serves to provide a firm grip between the plug and the sheath. This prevents inadvertent disconnection as a result of axial or parallel forces.

At the forward end of the housing 21 are a pair of parallel bifurcations 23 and 24 which define an elongated slot 25 therebetween. The rearward end of the slot 25 communicates with a central bore 26 that extends entirely through the rearward end of the housing 21 and is adapted to receive the forward end of the control wire 12.

Rigidly mounted to the bifurcations 23 and 24 and extending laterally across the slot 25 is a pivot pin 27. A stainless steel needle 28 with a barb 29 or spacer located thereon extends forwardly from the end of the housing 21 and its rearward end is rigidly mounted to the central portion of the pivot pin 27. The barbed needle 28 may not be used in some embodiments of the biopsy forceps, depending upon the particular application. The purpose of the barbed needle is to spear a sample of tissue and hold it in position to be cut and captured by the head assembly 20.

Figure 3:
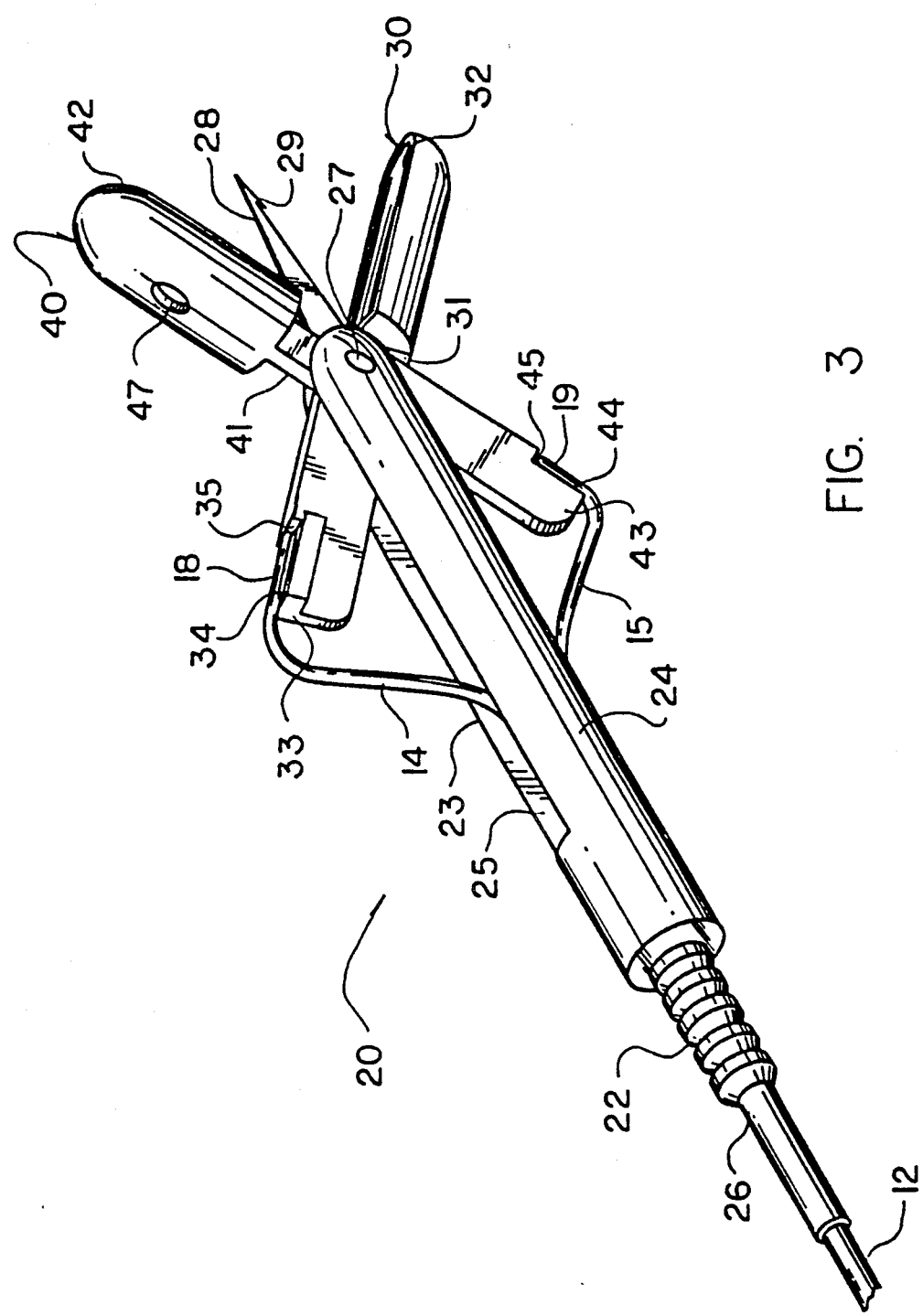
FIG. 3 is a fragmentary, perspective view of the biopsy forceps of FIGS. 1 and 2 showing the jaws in their open position and with the hollow sheath removed.

A pair of tongs or levers 30 and 40 are pivotally connected to the housing 21. These are shown pivoted to their open position in FIGS. 1 and 3 and to their closed position in FIGS. 2, 4, and 5. Each lever 30 and 40 has a front arm 31 and 41, respectively, which carries a cup or jaw 32, 42, which have relatively sharp edge portions that can be used to cut and capture a sample of tissue to be analyzed. The particular shape of the cup may vary from one embodiment of the invention to another to suit the particular application.

Each of the tongs also has a rearward arm 33, 43 connected to the front end 18, 19 of one of the two cable lengths 14 and 15. The rearward arms 33 and 43 are so shaped that when they are pivoted to the closed position (FIG. 2), they fit together side by side within the slot 25 and also accommodate the front ends 18 and 19 of the two cable lengths 14 and 15. The rear arms 33 and 43 have connector portions to receive the rearward ends of the cable lengths 14 and 15, which are soldered thereto to form a relatively rigid connection with the ends of the cable lengths extending generally parallel to the arms 33 and 43.

The rear arms have notches or platforms 34, 44 cut therein in planes extending longitudinally relative to the arms. The forward ends of these notches or platforms 34, 44 have a shoulder 35, 45 at their inner ends. The platforms 34 and 44 provide a seat for the ends of the cable lengths 14 and 15, which are soldered or welded in place thereon. The ends of the cable lengths 14 and 15 are positioned in abutment with the shoulders 35 and 45 to assure accurate positioning of the cable lengths. This arrangement assures that the effective operating portions of the cable lengths 14 and 15 that extend between the ends of the lever arms 33 and 43 and the Y-connector 13 are exactly the same.

The rearward arms 33 and 43 also have cooperating longitudinally extending flange portions 36 and 46 formed therein and extending inward from the respective inner side faces. When the levers 30 and 40 are moved to their closed position, these flange portions 36 and 46 engage one another to provide a limit position for the levers or tongs. This limit position is reached just as the jaws or cups reach their closed position. Accordingly, any additional force applied to the levers 30 and 40 by retraction of the control wire 12 will be transmitted to the flanges 36, 46 and not to the jaws or cups. This arrangement assures that any use of excessive retraction force will not result in damage to the cups or the forwardly extending lever arms.

It will also be noted that the cups 32 and 42 each have a central opening 37, 47 formed therein to permit the escape of liquid that could accumulate in the cups during the closing and tissue capturing movement.

Referring to FIG. 1, it will be apparent that because of the manner of connection of the cable lengths to the tongs, when the tongs are moved to their open position the cable lengths must bulge radially outward and make a gradual bend back into alignment with their inner ends, which are generally parallel to the control wire 12. The radial bulging, however, is limited so that it is no greater than the radial distance that the jaws 32 and 42 extend when in their open position. Accordingly, the radial bulging or bending of the cable lengths 14 and 15 will not displace the surrounding tissue any more than that caused by movement of the jaws.

The stiffness of the cable lengths must be carefully controlled so that the flexing of the cable lengths during the opening movement will not be unduly resisted. On the other hand, the cable lengths must be sufficiently stiff that forward movement of the control wire will transmit a sufficient compressive force relative to the lever arms to obtain sufficient opening of the jaws. The cable lengths actually serve to extend the length of the effective lever arm to which force is applied.

Referring to FIG. 1, it will be seen that the distance from the pivot axis to the general location at which force is applied by movement of the control wire, and thus the inner ends of the cable lengths, is significantly beyond the ends of the rearward arms 33 and 43. This feature enables the lever system to obtain optimum mechanical advantage in a minimum of available space.

The closing movement of the jaws 32 and 42 is obtained by retraction of the control wire relative to the housing 21. This pulls the cable lengths 14 and 15 in a rearward direction, thus moving the lever arms 33 and 43 inwardly to close the jaws in a position indicated in FIG. 2. It will be noted that in FIG. 2, the cable lengths are generally under tension rather than compression, and the resulting forces tend to hold the jaws 32 and 42 in their closed position with a sample of tissue captured therein.

The operating assembly 50 located at the rearward end of the hollow sheath 11 includes a hollow end cap 51 which is adapted for connection to the sheath 11, such as by swaging. The rear end of the hollow end cap 51 has a socket which receives a rear housing 52 with a thumb ring 53 formed at its outer end. The rear housing has a central, cylindrical body 54 with an axially extending slot 55 formed therein. Slidably located over the cylindrical body 54 is a hollow finger grip 60 with a lateral pin extending therethrough and received in the axial slot 55. The inner end of the control wire 12 is connected to the pin 61 so that axial movement of the finger grip 60 moves the control wire 12 in a longitudinal direction within the hollow sheath.

Thus, in the operation of the biopsy forceps thus described, the head assembly 20 is moved to its closed position by retracting the finger grip 60 and then inserted into the patient to a desired position for obtaining a sample of tissue. When the head assembly is so positioned, the finger grip 60 is moved forward relative to the thumb ring 53 to move the control wire forward and apply a compressive force against the cable lengths 14 and 15, causing them to bulge radially outward. This compressive force and resultant radial movement serve to open the tongs and move the cups or jaws to the open position shown in FIG. 1. At the same time, the needle 28 may be moved forward by further advance of the head assembly to spear a sample of tissue and retain it for capture.

With the jaws fully open, the operator moves the finger grip to the rear relative to the thumb ring to retract the control wire, and thus apply a tensile force to the cable lengths. This unflexes the cable lengths and causes closing of the jaws 32 and 42 to the position shown in FIG. 2. At the same time, a sample of tissue is cut by the closing motion and captured within the jaws or cups.

It will be noted that once the jaws or cups reach their closed position, the flanges 36 and 46 formed in the rearward arms 33 and 43 will engage one another to limit further movement of the tongs. Accordingly, when this condition is reached, any force applied to the control wire will be applied through the flanges 36 and 46 to the rearward ends of the tongs, and not to the cups or jaws.

Then, the head assembly is retracted, with the cups tightly held in their closed position by means of the finger grip 60 and the entire head assembly and hollow sheath are removed from the patient.

While the invention has been shown and described with respect to a specific embodiment thereof, this is intended for the purpose of illustration rather than limitation, and other variations and modifications of the specific embodiment herein shown and described will be apparent to those skilled in the art all within the intended spirit and scope of the invention. Accordingly, the patent is not to be limited in scope and effect to the specific embodiment herein shown and described nor in any other way that is inconsistent with the extent to which the state of the art has been advanced by the invention.

What is claimed is:

1. Biopsy forceps including a flexible sheath, a control wire extending through and movable within the sheath, a pair of cup-shaped jaws movable by the control wire to a closed position to capture a sample of tissue, and manual operating means connected at the rearward end of the sheath for extending and retracting the control wire linearly relative to said sheath, said forceps further comprising:
   an end housing connected to the forward end of said sheath and defining a central passage for receiving said control wire;
   a pair of tongs pivotally connected to the forward end of said housing and having said jaws connected to their respective outer ends, said tongs each having a rearwardly extending lever arm whereby said tongs are movable about a common pivot axis between a closed position wherein said jaws are closed to capture a sample of tissue and an open position wherein said jaws are open and said lever arms extend radially outward in opposite directions; and
   a pair of relatively stiff, flexible cable lengths connected at their inner ends to said control wire and rigidly connected at their outer ends respectively to said lever arms in coextensive relation therewith so that at least a portion of each cable length forms an extension of the respective lever arm, whereby when said control wire is retracted by said manual operating means, said lever arms are moved to their closed position and when said control wire is extended by said manual operating means said cable lengths flex outwardly in opposite directions to move said lever arms to their open position.

2. A device as defined in claim 1, wherein said end housing has a pair of forwardly extending bifurcations defining a slot therebetween that communicate with said central passage, said pivot axis extending across said slot between said bifurcations.

3. A device as defined in claim 1, wherein said cable lengths are formed of stranded stainless steel wire.

4. A device as defined in claim 1, wherein said rearwardly extending lever arms define a platform facing radially outward parallel to the pivot axis and a shoulder at the inner end of said platform, said forward portions of said cable lengths being fastened to said platforms with their ends butting against said shoulders.

5. A device as defined in claim 4, wherein said cable lengths are formed of stranded stainless steel wire filaments and are soldered to said platforms.

6. A device as defined in claim 1, wherein the rearward end of said end housing has a rearwardly extending plug portion with circumferential barbs formed thereon and being adapted to receive the forward end of said sheath.

7. A device as defined in claim 6, wherein the end portion of said sheath received on said plug has internal threads formed therein.

8. A device as defined in claim 1, wherein the rearward end of each of said lever arms is provided with a stop means, said respective stop means of said arms being adapted to engage one another when said tongs are moved to their closed position whereby any additional retraction force applied through said control wire will be applied only to said stop means.

9. A device as defined in claim 8, wherein said stop means comprise flanges formed on said rearward lever arms and extending inwardly from the inner sides of said lever arms whereby they engage one another when said tongs are closed.

10. Biopsy forceps including a flexible sheath, a control wire extending through and movable within the sheath, a pair of cup-shaped jaws movable by the control wire to a closed position to capture a sample of tissue, and manual operating means connected at the rearward end of the sheath for extending and retracting the control wire linearly relative to said sheath, said forceps further comprising:
  an end housing connected to the forward end of said sheath and defining a central passage for receiving said control wire;
  pivot means in the forward end of said end housing;
  a pair of tongs pivotally connected to the forward end of said housing by said pivot means and having said jaws connected to their respective outer ends, said tongs each having a rearwardly extending lever arm whereby said tongs are movable between a closed position wherein said jaws are closed to capture a sample of tissue and an open position wherein said jaws are open and said lever arms extend radially outward in opposite directions; and
  a pair of relatively stiff, flexible cable lengths connected at their inner ends to said control wire and rigidly connected at their outer ends respectively to said lever arms,
  means formed on each rearward lever arm defining an axially extending, outwardly facing surface parallel to said pivot axis and means defining an outwardly extending shoulder at the inward end of said axially extending surface, whereby the outward portion of each cable length may be secured to a respective axially extending surface with its inner end abutting said shoulder,
  whereby when said control wire is retracted by said manual operating means, said lever arms are moved to their closed position and when said control wire is extended by said manual operating means said cable lengths flex outwardly in opposite directions to move said lever arms to their open position.

11. A device as defined in claim 10, wherein said end housing has a pair of forwardly extending bifurcations defining a slot therebetween that communicate with said central passage, said pivot axis extending across said slot between said bifurcations.

12. A device as defined in claim 10, wherein said cable lengths are formed of stranded stainless steel wire.

13. A device as defined in claim 10, wherein the rearward end of said end housing has a rearwardly extending plug portion with circumferential barbs formed thereon and being adapted to receive the forward end of said sheath.

14. A device as defined in claim 13, wherein the end portion of said sheath received on said plug has internal threads formed therein.

15. A device as defined in claim 10, wherein the rearward end of each of said lever arms is provided with a stop means, said respective stop means of said arms being adapted to engage one another when said tongs are moved to their closed position whereby any additional retraction force applied through said control wire will be applied only to said stop means.

16. A device as defined in claim 15, wherein said stop means comprise flanges formed on said rearward lever arms and extending inwardly from the inner sides of said lever arms whereby they engage one another when said tongs are closed.

* * * * *

UNITED STATES PATENT AND TRADEMARK OFFICE
CERTIFICATE OF CORRECTION

PATENT NO. : 5,082,000

DATED : January 21, 1992

INVENTOR(S) : George J. Picha; Dean J. Secrest

It is certified that error appears in the above-identified patent and that said Letters Patent is hereby corrected as shown below:

On the title page:  Section [54], "CALDE" should be --CABLE--.

In Column 1, Line 2, "CALDE" should be -- CABLE--.

Signed and Sealed this

First Day of June, 1993

Attest:

MICHAEL K. KIRK

*Attesting Officer*   *Acting Commissioner of Patents and Trademarks*